United States Patent [19]
Jakob et al.

[11] Patent Number: 4,873,326

[45] Date of Patent: Oct. 10, 1989

[54] PROCESS FOR THE PREPARATION OF N-ALKYLATED CAPROLACTAMS

[75] Inventors: Wolfgang Jakob, Moers; Wolfgang Alewelt; Erhard Tresper, both of Krefeld, all of Fed. Rep. of Germany

[73] Assignee: Bayer Aktiengesellschaft, Leverkusen Bayerwerk, Fed. Rep. of Germany

[21] Appl. No.: 231,232

[22] Filed: Aug. 11, 1988

[30] Foreign Application Priority Data

Aug. 15, 1987 [DE] Fed. Rep. of Germany ....... 3727255
Oct. 23, 1987 [DE] Fed. Rep. of Germany ....... 3735904

[51] Int. Cl.$^4$ ............................................ C07D 223/10
[52] U.S. Cl. .................................... 540/538; 540/485; C07D/223/10
[58] Field of Search ................................ 540/538, 485

[56] References Cited

U.S. PATENT DOCUMENTS

3,988,319 10/1976 Mares .................................. 540/538
4,767,587 8/1988 Merger et al. ...................... 540/538

FOREIGN PATENT DOCUMENTS

1944910 4/1970 Fed. Rep. of Germany ...... 540/538
2131199 1/1972 Fed. Rep. of Germany ...... 540/538

OTHER PUBLICATIONS

Journal of the American Chemical Society, 94:Kirk et al (1972).
Mechanismen und Theorie in der Organischen Chemie, Lowry et al (1980).

Primary Examiner—Robert T. Bond
Attorney, Agent, or Firm—Connolly and Hutz

[57] ABSTRACT

This invention relates to a process for the preparation of N-alkylated caprolactams by the cyclization of N-alkylated caproic acids.

3 Claims, No Drawings

PROCESS FOR THE PREPARATION OF N-ALKYLATED CAPROLACTAMS

This invention relates to a process for the preparation of N-alkylated caprolactams by the cyclisation of N-alkylated caproic acids.

N-alkylated caprolactams belong to the group of aprotic dipolar solvents and are frequently used for carrying out chemical syntheses, especially on a large technical scale. They are preferably used, for example, for the preparation of polyarylenesulphides (e.g. EP-OS 171 021).

N-alkylated caprolactams have the advantage over other solvents such as pyrrolidones that they have higher boiling points. This means that if a high reaction temperature is required, this can be obtained at normal pressure when an N-alkylated caprolactam is used as solvent so that the process, e.g. on a large technical scale, can be carried out more economically.

In the presence of alkalies, however, N-alkylated caprolactams are partly decomposed and N-alkylaminocaproates are formed as unwanted by-products.

The partial cyclisation of N-alkylaminocaproic acids to N-alkylcaprolactams by heating the acids above their melting point and at the same time distilling off lactam and water has been disclosed in Am. Soc. 70 (1948) 2118 but the yields are only about 80% and therefore too low for processes carried out on a technical scale.

It has now been found that N-alkylcaprolactams can be obtained in yields of over 95% by the cyclisation of N-alkylated caproic acids and N-alkylaminocaproates by adjusting their solutions to the isoelectric point of the particular N-alkylaminocaproic acid and heating to about 230° C. and optionally distilling.

It was not to be expected that N-alkylated lactams could be prepared almost quantitatively from N-alkylaminocaproic acids or their salts by cyclisation since the formation of 7-membered rings by cyclisation is difficult to achieve and only with insufficient yields.

The process according to the invention in particular enables N-alkylcaprolactams to be recovered from the mother liquors of chemical reactions which contain N-alkylaminocaproates and the free acids.

This invention therefore relates to a process for the preparation of N-alkylcaprolactams by cyclisation of N-alkylaminocaproic acids or their salts, characterised in that solutions of N-alkylaminocaproic acids or their salts in the corresponding N-alkylaminocaprolactams adjusted to the isoelectric point of the N-alkylaminocaproic acid, the solutions are briefly heated to the boiling point o the N-alkylaminocaprolactam, and after removal of the water of reaction by distillation the N-alkylaminocaprolactam is optionally directly returned to a reaction solution or the lactam is separated by distillation and purified.

The N-alkylaminocaproic acids used may be acids or their salts corresponding to formula (I):

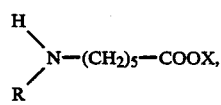

wherein
$R^1$ stands for $C_1$–$C_{20}$-alkyl or $C_5$–$C_{50}$-cycloalkyl and
X stands for H or a cation such as ammonium, Li, Na, K, ½ Ca or ½ Mg.

N-methylaminocaproic acid and its sodium salt are preferred.

In the process according to the invention, the reaction solution is heated to a temperature of 180°–300° C., preferably 200°–240° C., especially 230° C., after it has been adjusted to the isoelectric point of the amino acid. The pressure employed is from 0.04 to 40 bar and is preferably the pressure which is established by the vapour pressure of the solution, and normal pressure is particularly preferred.

The concentration of the N-alkylaminocaproic acids or their salts in the corresponding N-alkylcaprolactams may be from 0.1 to 90% by weight and is preferably from 5 to 20% by weight, especially from 10 to 15% by weight.

EXAMPLES

COMPARISON EXAMPLE 1

50 g of N-methylaminocaproic acid are heated to 250° C. in a 100 ml three-necked flask equipped with internal thermometer and descending condenser. 5.8 g of water distil off. The contents of the flask are then cooled and the N-methylcaprolactam formed is distilled off at about 0.3 bar. 33.7 g of distillate (77% yield) which is identified gas chromatographically and IR spectroscopically as N-methylcaprolactam and 9.7 g of undistillable residue are obtained.

COMPARISON EXAMPLE 2

50 g of sodium N-methylaminocaproate were treated as described in Example 1. No distillate could be obtained and the residue amounted to 49.9 g.

50 g of N-methylaminocaproic acid were dissolved in 100 g of N-methylcaprolactam and heated to 230° C. for 3 hours in a 250 ml three-necked flask equipped with internal thermometer and descending condenser. 3.0 g of water distilled off. The contents of the flask were then cooled and distilled to a sump temperature of 245° C. at about 0.3 bar. 121 g (96% yield) of distillate were obtained. The residue amounted to 0.6 g.

EXAMPLE 2

30 g of Sodium N-methylaminocaproate were suspended in 100 g of N-methylcaprolactam in a 250 ml three-necked flask equipped with internal thermometer and descending condenser. 36 ml of 5N hydrochloric acid were added to 30 the suspension. The resulting solution had a pH of 6.7. 122 g (96.5%) of N-methylcaprolactam were obtained after distillation as in Example 1.

We claim:
1. Process for the preparation of N-alkylcaprolactams by the cyclisation of N-alkylaminocaproic acids or their salts, characterised in that solutions of N-alkylaminocaproic acids or their salts in the corresponding N-alkylaminocaprolactams are adjusted to the isoelectric point of the N-alkylaminocaproic acid, the solutions are briefly heated to the boiling point of the N-alkylaminocaprolactam and after removal of the water of reaction by distillation the N-alkylaminocaprolactam is optionally directly returned to a reaction solution or the lactam is separated by distillation and purified.

2. Process according to claim 1, characterised in that cyclisation is carried out at a temperature from 180 to 300° C. and at pressures of from 0.01 to 40 bar.

3. Process according to claim 1, characterised in that the N-alkylaminocaproic acid which is to be cyclised is present in the N-alkylaminocaprolactam at a concentration of 0.1 to 90% by weight.